US009200241B2

(12) United States Patent
Dente et al.

(10) Patent No.: US 9,200,241 B2
(45) Date of Patent: Dec. 1, 2015

(54) MALODOR NEUTRALIZING COMPOSITIONS COMPRISING BORNYL ACETATE OR ISOBORNYL ACETATE

(75) Inventors: Stephen V. Dente, Oakland, NJ (US); Ketrin Leka Basile, Bronx, NY (US); Brian Fielder, Leonia, NJ (US); Garry Johnson, Allendale, NJ (US)

(73) Assignee: Robertet, Inc., Mount Olive, NJ (US)

( * ) Notice: Subject to any disclaimer, the term of this patent is extended or adjusted under 35 U.S.C. 154(b) by 55 days.

(21) Appl. No.: 13/356,011

(22) Filed: Jan. 23, 2012

(65) Prior Publication Data

US 2012/0237469 A1 Sep. 20, 2012

Related U.S. Application Data

(60) Provisional application No. 61/436,787, filed on Jan. 27, 2011.

(51) Int. Cl.
| | | |
|---|---|---|
| *C11D 3/50* | (2006.01) |
| *A61L 9/01* | (2006.01) |
| *A61K 8/36* | (2006.01) |
| *A61K 8/37* | (2006.01) |
| *A61Q 19/00* | (2006.01) |

(52) U.S. Cl.
CPC ... *C11D 3/50* (2013.01); *A61K 8/36* (2013.01); *A61K 8/37* (2013.01); *A61L 9/01* (2013.01); *A61Q 19/00* (2013.01); *A61K 2800/10* (2013.01)

(58) Field of Classification Search
None
See application file for complete search history.

(56) References Cited

U.S. PATENT DOCUMENTS

| | | |
|---|---|---|
| 4,000,329 A | 12/1976 | Pittet et al. |
| 4,009,253 A | 2/1977 | Schleppnik et al. |
| 4,010,253 A | 3/1977 | Reese et al. |
| 4,107,289 A | 8/1978 | Kaufman |
| 4,310,152 A | 1/1982 | Mitzel |
| 5,089,258 A | 2/1992 | Zaid |
| 5,098,694 A | 3/1992 | Komp et al. |
| 5,198,144 A | 3/1993 | Ichii et al. |
| 5,202,124 A | 4/1993 | Williams et al. |
| 5,451,346 A | 9/1995 | Amou et al. |
| 5,554,588 A | 9/1996 | Behan et al. |
| 5,589,164 A | 12/1996 | Cox et al. |
| 5,662,937 A | 9/1997 | McCuaig |
| 5,676,163 A | 10/1997 | Behan et al. |
| 5,720,947 A | 2/1998 | Basset et al. |
| 5,795,566 A | 8/1998 | Joulain et al. |
| 5,800,897 A | 9/1998 | Sharma et al. |
| 6,019,855 A | 2/2000 | Finch et al. |
| 6,495,097 B1 | 12/2002 | Streit et al. |
| 6,753,308 B1 | 6/2004 | Richardson et al. |
| 6,906,045 B2 | 6/2005 | Ebube et al. |
| 7,147,822 B2 | 12/2006 | Parkhurst et al. |
| 7,157,411 B2 | 1/2007 | Rohde et al. |
| 7,261,742 B2 | 8/2007 | Leskowicz |
| 7,407,515 B2 | 8/2008 | Leskowicz |
| 7,407,922 B2 | 8/2008 | Leskowicz |
| 7,569,232 B2 | 8/2009 | Man et al. |
| 7,638,118 B2 | 12/2009 | Flachsmann et al. |
| 2002/0197287 A1 | 12/2002 | Streit et al. |
| 2003/0113289 A1 | 6/2003 | Hu et al. |
| 2004/0091595 A1 | 5/2004 | Dewis et al. |
| 2004/0221858 A1 | 11/2004 | Higashi et al. |
| 2006/0228250 A1 | 10/2006 | Brown et al. |
| 2006/0287219 A1 | 12/2006 | Dykstra et al. |
| 2007/0054815 A1 | 3/2007 | Convents et al. |
| 2007/0231278 A1 | 10/2007 | Lee et al. |
| 2008/0207481 A1 | 8/2008 | Meine et al. |
| 2008/0221003 A1 | 9/2008 | Meine et al. |
| 2010/0021413 A1 | 1/2010 | McGee et al. |
| 2010/0028288 A1 | 2/2010 | Tranzeat et al. |
| 2010/0034766 A1 | 2/2010 | McGee et al. |
| 2010/0111889 A1 | 5/2010 | Marsh et al. |
| 2011/0239736 A1 | 10/2011 | Ramji et al. |
| 2011/0305659 A1 | 12/2011 | Woo et al. |

FOREIGN PATENT DOCUMENTS

| | | | |
|---|---|---|---|
| AU | 2009101152 | 1/2010 | |
| DE | 3045483 A1 * | 12/1982 | ............ A61K 35/78 |
| GB | 801726 A | 9/1958 | |
| GB | 1311060 | 3/1973 | |
| GB | 2187642 | 9/1987 | |
| JP | 63-066115 | 3/1988 | |
| JP | 7-291809 | 11/1995 | |
| JP | 2000-282081 A * | 10/2000 | ............... C11D 1/29 |
| WO | WO 97/15283 | 5/1997 | |
| WO | WO 98/56889 | 12/1998 | |
| WO | WO 00/27442 | 5/2000 | |
| WO | WO 00/72890 | 12/2000 | |
| WO | WO 03/051410 | 6/2003 | |
| WO | WO 2006/102052 | 9/2006 | |
| WO | WO 2006/131739 | 12/2006 | |
| WO | WO 2011/152886 | 12/2011 | |

OTHER PUBLICATIONS

Matsubara et al., "(-)-Bornyl acetate induces autonomic relaxation and reduces arousal level after visual display terminal work without any influences of task performance in low-dose condition.", Biomed Res., 32(2), pp. 151-157 (Apr. 2011) (Abstract).*

(Continued)

*Primary Examiner* — Bethany Barham
*Assistant Examiner* — Barbara Frazier
(74) *Attorney, Agent, or Firm* — Fish & Richardson P.C.

(57) ABSTRACT

Composition comprising bornyl or isobornyl acetate and certain acids are effective for reducing malodors. The acids have the formula R—COOH in which R is $C_{1-5}$ alkyl or R is $C_3$ or $C_4$ alkylene optionally phenyl-substituted. These compositions can be used in perfumed products, household products and personal care products.

22 Claims, No Drawings

(56) References Cited

OTHER PUBLICATIONS

English Abstract, JP 2000-282081 (2000).*
English Abstract, DE 3045483 (1982).*
Machine translation, JP 2000-282081 (2000).*
International Search Report and Written Opinion mailed in corresponding application No. PCT/US2012/022209 on Apr. 4, 2012.
International Preliminary Report on Patentability mailed in corresponding International Application No. PCT/US2012/022209 on Aug. 8, 2013.
International Search Report dated Aug. 19, 2013 issued in related PCT Application No. PCT/US2013/033927.
International Preliminary Report on Patentability mailed in corresponding International Application No. PCT/US2011/022697 on Dec. 13, 2012.
International Search Report and Written Opinion mailed in corresponding International Application No. PCT/US2011/022697 on Jul. 5, 2012.
International Search Report and Written Opinion mailed on Nov. 14, 2013 in International Application No. PCT/US2013/033927.

* cited by examiner

MALODOR NEUTRALIZING COMPOSITIONS COMPRISING BORNYL ACETATE OR ISOBORNYL ACETATE

CROSS-REFERENCE TO RELATED APPLICATION

This application claims the benefit of the filing date of U.S. Provisional Application No. 61/436,787 filed on 27 Jan. 2011. The contents of said provisional application are incorporated by reference in their entirety as part of this application.

FIELD OF THE INVENTION

This invention relates to odor neutralizer compositions and their use for reducing malodors.

BACKGROUND OF THE INVENTION

In many applicational areas, perfumes are used for masking malodors. Annoyance caused by malodors occurs frequently in daily life and impairs personal well-being. Such malodors are, for example, those resulting from substances transpired or excreted by humans, in particular, perspiration, mouth odors, feces and urine, odors caused by animal feces or urine, in particular, those of domestic pets, kitchen odors, such as those resulting from the preparation of onions, garlic, cabbage or fish, odors due to tobacco smoke, garbage, bathrooms, molds and waste.

In addition, malodors may be caused by many industrially produced basic materials used in cleansing agents, such as, for example, detergents and fabric softeners, or in body care products, such as, for example, soaps and cosmetics. The use of specific cosmetic preparations, such as, for example, hair dyes, hair-forming agents and depilatories, also produce malodors.

Many rubber and plastic products also produce malodors if, due to the method of their manufacture, they still contain quantities of highly odorous, volatile active ingredients. These malodors are usually caused by particularly odorous substances which are, however, generally only present in trace amounts. Such substances include, for example, nitrogen-containing compounds such as ammonia and amines, heterocyclic compounds such as pyridines, pyrazines, indoles, etc., and sulfur-containing compounds such as hydrogen sulfide, mercaptans, sulfides, etc.

The masking of malodors is a problem which is difficult to handle and solve with perfume compositions. Usually, it is only possible to mask malodors by means of a specially developed perfume oil having specific types of fragrances.

Malodor counteracting compositions are particularly advantageous when they are capable of reducing the intensity of malodors without themselves possessing any significantly intense odor or fragrance. Such active ingredients do not mask malodors; rather, they neutralize the malodors. This has the advantage that, when using such active ingredients for perfuming objects or products having malodors, perfume oils of any desired type of fragrance can be used. The consumer can, therefore, be offered a considerably broader range of fragrance types for combating malodors.

In addition, active ingredients which neutralize malodors, provide the possibility of reducing the quantity of perfume oil previously required for masking odors. It is also possible to use less intensely odorous perfumes for combating malodors than those heretofore employed.

Another area in which malodor reducing compositions find utility is in breath freshening compositions such as chewing gum, mints, mouthwashes, lozenges and sprays. In addition to flavoring and perfuming ingredients which mask oral malodors, it is also useful to neutralize the ingredients which cause such malodors.

In recent years, a wide variety of substances have been proposed for use in neutralizing malodors, including some substances traditionally used as perfumes and/or as ingredients in deodorizing compositions. Bornyl acetate and isobornyl acetate are well-known perfuming ingredients and have been used in deodorizing compositions and to lend a pleasing scent to various types of consumer products. Examples of such uses are shown in U.S. Pat. Nos. 5,198,144, 5,451,346, 5,554,588, 6,019,855 and 7,569,232 and in Patent Application Publication US 2006/0228250. More recently, the use of bornyl acetate and isobornyl acetate, separately and together, has been disclosed in Patent Application Publications US 2008/0207481 and US 2008/0221003, as ingredients in compositions intended to exhibit varying discernable odors.

It has now been discovered that, although bornyl acetate and isobornyl acetate have some odor-neutralizing effect and can be considered as malodor counteractants, combinations of bornyl or isobornyl acetate with certain low molecular weight monocarboxylic acids have shown surprising enhanced effectiveness in neutralizing malodors. Although the acids themselves may possess a characteristic odor, in combination with bornyl acetate or isobornyl acetate they act as agents to neutralize malodors.

SUMMARY OF THE INVENTION

This invention provides a combination of bornyl acetate or isobornyl acetate and a monocarboxylic acid of the Formula (I):

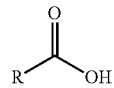

in which R is $C_1$-$C_5$ alkyl or R is $C_3$ or $C_4$ alkylene optionally substituted by phenyl.

DETAILED DESCRIPTION OF THE INVENTION

Bornyl acetate has the formula

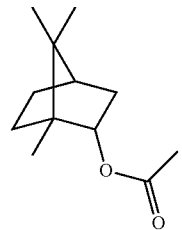

endo-1,7,7-trimethylbicyclo[2.2.1]heptan-2-yl acetate

Isobornyl acetate has the formula

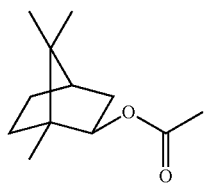

exo-1,7,7-trimethylbicyclo[2.2.1]heptan-2-yl acetate

The acids used in the compositions of this invention have the general formula

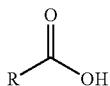

In which R is $C_1$-$C_5$ alkyl or R is $C_3$ or $C_4$ alkylene optionally substituted by phenyl. These alkyl and alkylene groups can be branched or unbranched. An example of a phenyl-substituted acid is cinnamic acid.

In order to combat malodors, the combination of bornyl or isobornyl acetate and the acids of Formula (I) may be used in admixture. They may be used in pure form or in suitable solvents such as, for example, ethanol, isopropanol or other solvents well known for use in deodorizing formulations.

The ratio of bornyl or isobornyl acetate to the acid of Formula (I) can range between about 10% to 90%, preferably from about 25% to 75%. A weight ratio of about 50% is particularly preferred and convenient.

Preferred acids within the Formula (I) include the following:

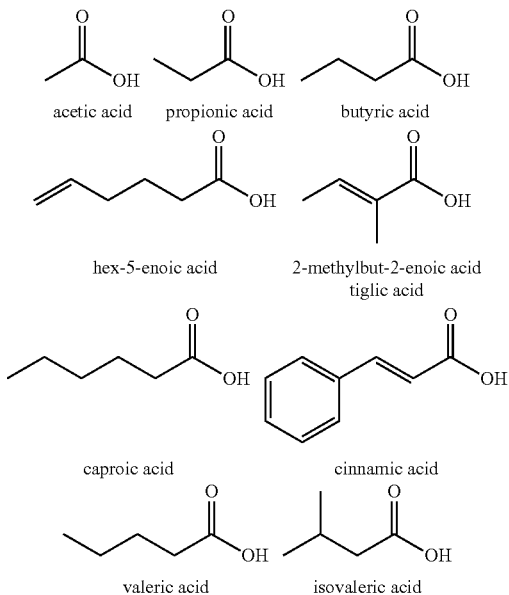

In odor neutralizers, the compositions comprising bornyl or isobornyl acetate and one or more of these acids according to the present invention can be combined with one or more of a wide variety of fragrances.

The following may be mentioned as examples of ingredients used in fragrancing compositions, in particular:

extracts from natural raw materials such as essential oils, resins, resinoids, balsams, tinctures such as for example ambergris tincture; amyris oil; angelica seed oil; angelica root oil; aniseed oil; valerian oil; basil oil; tree moss absolute; bay oil; armoise oil; benzoe resinoid; bergamot oil; beeswax absolute; birch tar oil; bitter almond oil; savory oil; buchu leaf oil; cabreuva oil; cade oil; calamus oil; camphor oil; cananga oil; cardamom oil; cascarilla oil; cassia oil; cassie absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; eau de brouts absolute; oakmoss absolute; elemi oil; estragon oil; eucalyptus citriodora oil; eucalyptus oil (cineole type); fennel oil; fir needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calamus oil; blue camomile oil; Roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil expressed; linaloe oil; Litsea cubeba oil; laurel leaf oil; mace oil; marjoram oil; mandarin oil; massoi (bark) oil; mimosa absolute; ambrette seed oil; musk tincture; clary sage oil; nutmeg oil; myrrh absolute; myrrh oil; myrtle oil; clove leaf oil; clove bud oil; neroli oil; olibanum absolute; olibanum oil; opopanax oil; orange flower absolute; orange oil; origanum oil; palmarosa oil; patchouli oil; perilla oil; Peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmatian sage oil; Spanish sage oil; sandalwood oil; celery seed oil: spikelavender oil; star anise oil; storax oil; tagetes oil; fir needle oil; tea tree oil; turpentine oil; thyme oil; Tolu balsam; tonka bean absolute; tuberose absolute; vanilla extract; violet leaf absolute; verbena oil; vetiver oil; juniperberry oil; wine lees oil; wormwood oil; wintergreen oil; ylang-ylang oil; hyssop oil; civet absolute; cinnamon leaf oil; cinnamon bark oil; and fractions thereof or ingredients isolated therefrom;

individual fragrance ingredients from the group comprising hydrocarbons, such as for example 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

aliphatic alcohols, such as for example hexanol; octanol; 3-octanol; 2,6-dimethyl-heptanol; 2-methyl-2-heptanol, 2-methyl-2-octanol; (E)-2-hexenol; (E)- and (Z)-3-hexenol; 1-octen-3-ol; a mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; aliphatic aldehydes and their acetals such as for example hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal-diethylacetal; 1,1-dimethoxy-2,2,5-trimethyl-4-hexene; citronellyl oxyacetaldehyde;

aliphatic ketones and oximes thereof, such as for example 2-heptanone; 2-octanone; 3-octanone; 2-nonanone; 5-methyl-3-heptanone; 5-methyl-3-heptanone oxime; 2,4,4,7-tetramethyl-6-octen-3-one;

aliphatic sulfur-containing compounds, such as for example 3-methylthiohexanol; 3-methylthiohexyl acetate; 3-mercaptohexanol; 3-mercaptohexyl acetate; 3-mercaptohexyl butyrate; 3-acetyltbiohexyl acetate; 1-menthene-8-thiol;

aliphatic nitriles, such as for example 2-nonenenitrile; 2-tridecenenitrile; 2,12-tridecenenitrile; 3,7-dimethyl-2,6-octadienenitrile; 3,7-dimethyl-6-octenenitrile;

aliphatic carboxylic acids other than those included in Formula (I) and esters of aliphatic acids, such as for example (E)- and (Z)-3-hexenylformate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexylbutyrate; (E)- and (Z)-3-hexenyl isobutyrate; hexyl crotonate; ethylisovalerate; ethyl-2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyl oxyacetate; methyl-3,7-dimethyl-2,6-octadienoate;

acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof;

acyclic terpene aldehydes and ketones, such as, for example, geranial; neral; citronellal; 7-hydroxy-3,7-dimethyloctanal; 7-methoxy-3,7-dimethyloctanal; 2,6,10-trimethyl-9-undecenal; α-sinensal; β-sinensal; geranylacetone; as well as the dimethyl- and diethylacetals of geranial, neral and 7-hydroxy-3,7-dimethyloctanal;

cyclic terpene alcohols, such as, for example, menthol; isopulegol; alpha-terpineol; terpinen-4-ol; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates and 3-methyl-2-butenoates of alpha-terpineol; terpinen-4-ol; menthan-8-ol, menthan-1-ol, methan-7-ol, borneol, isoborneol, linalool oxide, nopol, cedrol, ambrinol, vetiverol and guaiol; cyclic terpene aldehydes and ketones, such as, for example, menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alphadamascone; beta-damascone; beta-danascenone; deltadamascone; gamma-damascone; 1-(2,4,4-trimethyl-2-cyclohexen-1-yl)-2-buten-1-one; 1,3,4,6,7,8a-hexahydrol; 1,1,5,5-tetramethyl-2H-2,4a-methanonaphthalen-8(5H)-one; nootkatone; dihydrootkatone; acetylated cedarwood oil (cedryl methyl ketone);

cyclic alcohols, such as, for example, 4-tert.-butylcyclohexanal; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

cycloaliphatic alcohols, such as, for example, alpha-3,3-trimethylcyclo-hexyl-methanol; 2-methyl-4-(2,2,3-trimethyl-3-cyclopent-1-yl)-butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)-pentan-3-ol; 1-(2,2,6-trimethylcyclohexyl)-hexan-3-ol;

cyclic and cycloaliphatic ethers, such as, for example, cineole; cedryl methyl ether; cyclododecyl methyl ether; (ethoxymethoxy)-cyclododecane; alpha-cedrene epoxide; 3a,6,6,9a-tetramethyldodecahydronaphtho[2,1-b]furan; 3a-ethyl-6,6,9a-trimethyl-dodecahydronaphtho[2,1-b]furan; 1,5,9-trimethyl-13-oxabicyclo[10.1.0]-trideca-4,8-diene; rose oxide; 2-(2,4-dimethyl-3-cyclohexen-1-yl)-5-methyl-5-(1-methyl-propyl)-1,3-dioxan;

cyclic ketones, such as, for example, 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-lone; 6,7-dihydro-1,1,2,3,3-pentamethyl-4(5H)-indanone; 5-cyclohexadecen-1-one; 8-cyclohexadecen-1-one; 9-cycloheptadecen-1-one; cyclopentadecanone; cycloaliphatic aldehydes, such as, for example, 2,4-dimethyl-3-cyclohexene carbaldehyde; 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

cycloaliphatic ketones, such as, for example, 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphtalenyl methyl ketone; methyl-2,6,10-trimethyl-2,5,9-cyclododecatrienyl ketone; tert.-butyl-(2,4-dimethyl-3-cyclohexen-1-yl)-ketone;

esters of cyclic alcohols, such as, for example, 2-tert.butylcyclohexyl acetate; 4-tert.-butylcyclohexyl acetate; 2-tert.-pentylcyclohexyl acetate; 4-tert.-pentylcyclohexyl acetate; decahydro-2-naphthyl acetate; 3-pentyltetrahy-dro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

esters of cycloaliphatic carboxylic acids, such as, for example, allyl 3-cyclohexyl-propionate; allyl cyclohexyl oxyacetate; methyl dihydrojasmonate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1dimethyl-3-phenylpropanol; 1-ethyl-1-methyl-3-phenylpropanol; 2-methyl-5-phenylpentanol;

3-methyl-5-phenylpentanol; 3-phenyl-2-propen-1-ol; 4-methoxybenzyl alcohol; 1-(4-isopropylphenyl)ethanol;

esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

araliphatic ethers, such as for example, 2-phenylethyl methyl ether; 2-phenylethyl isoamyl ether; 2-phenylethyl-1-ethoxyethyl ether; phenylacetaldehyde dimethyl acetal; phenylacetaldehyde diethyl acetal; hydratropaaldehyde dimethyl acetal; phenyl acetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

aromatic and araliphatic aldehydes, such as, for example, benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethyl-proparral; 2-methyl-3-(4-isopropylphenyl)-propanal; 2-methyl-3-(4-tert.-butylphenyl)propanal; 3-(4-tert.-butyl-phenyl)propanal; cinnamaldehyde; alphabutyl-cinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylene-dioxybenzaldehyde; 3,4-dimethoxybenzaldehyde; 2-methyl-3-(4-methoxyphenyl)-propanal; 2-methyl-3-(4-methylendioxyphenyl)-propanal;

aromatic and araliphatic ketones, such as, for example, acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6hexamethyl-5-indanyl methyl ketone; 6-tert.-butyl-1,1,1-dimethyl-4-indanyl methyl ketone; 1-[2,3-dihydro-1,1,2,6-tetramethyl-3-(1-methyl-ethyl)-1H-5-indenyl]ethanone; 5',6',7',8'-tetrahydro-3',5',5',6',8',8'-hexamethyl-2-acetonaphthone;

aromatic and araliphatic carboxylic acids and esters thereof, such as, for example, benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

nitrogen-containing aromatic compounds, such as, for example, 2,4,6-trinitro-1,3-dimethyl-5-tert-butylbenzene; 3,5-dinitro-2,6-dimethyl-4-tert.-butylacetophenone; cinnamonitrile; 5-phenyl-3-methyl-2-pentenonitrile; 5-phenyl-3-methylpentanonitrile; methyl anthranilate; methyN-methylanthranilate; Schiff's bases of methyl anthranilate with 7-hydroxy-3,7-dimethyloctanal, 2-methyl-3-(4-tert.-butylphenyl)-propanal or 2,4-dimethyl-3-cyclohexene carbaldehyde; 6-isopropylquinoline; 6-isobutylquinoline; 6-sec.-butylquinoline; indole; skatole; 2-methoxy-3-isopropyl-pyrazine; 2-isobutyl-3-methoxypyrazine;

phenols, phenyl ethers and phenyl esters, such as, for example, estragole; anethole; eugenol; eugenyl methyl ether; isoeugenol; isoeugenol methyl ether; thymol; carvacrol; diphenyl ether; beta-naphthyl methyl ether; betanaphthyl ethyl ether; beta-naphthyl isobutyl ether; 1,4-dimethoxybenzene; eugenyl acetate; 2-methoxy-4-methylphenol; 2-ethoxy-5-(1-propenyl)-phenol; p-cresyl phenylacetate;

heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-1'-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; coumarin; 2,3-dihydrocoumarin; octahydrocoumarin.

In addition, the odor neutralizers according to the present invention can be adsorbed onto a carrier which ensures both the fine distribution of the odor neutralizer in the product and controlled release during use. Such carriers can be porous inorganic materials such as light sulfate, silica gels, zeolites, gypsums, clays, granulated clays, aerated concrete, etc., or organic materials such as wood and other cellulose-based materials.

The odor neutralizers containing bornyl or isobornyl acetate and acids of Formula (I) can also be in microencapsulated or spray-dried form or in the form of inclusion complexes or extrusion products and they can be added in these forms to the product whose odor is to be improved or which is to be perfumed.

The compositions of the present invention may be added to a wide variety of consumer products, such as household products, personal care products and cosmetics, both perfumed and perfume-free.

Household products which may comprise a composition according to the invention include fabric washing powder and washing liquid, detergent, surface cleaner (including hard surface cleaner), air freshener, softener, bleach, fabric refresher and room spray, disinfection products, scourer and cat litter. The list of household products is given by way of illustration and is not to be regarded as being in any way limiting.

Personal care products and cosmetics which may comprise a composition according to the invention include lotion, e.g. after-shave lotion, shampoo, conditioner, styling spray, mousse, gel, hair wipe, hair spray, hair pomade, bath and shower gel, bath salt, hygiene products, deodorant, antiperspirant, breath-freshening sprays, breath-freshening chewing gum, mouthwashes, lozenges and mints, vanishing cream, depilatory, and talcum powder. The list of personal care products and cosmetics is given by way of illustration and is not to be regarded as being in any way limiting.

Typically, the products using the composition of this invention comprise from about 0.0001% to about 20% by weight, preferably about 0.001% to about 10% by weight, of bornyl or isobornyl acetate and at least one acid of Formula (I) based on the product. The effective amount depends upon the type of product into which the combination is admixed.

For example, if used in a fabric refresher the combination may be added to a fragrance composition at around 1% by weight which is then added to the product at around 0.1% by weight, i.e. the fabric refresher comprises about 0.001% by weight of the composition as hereinabove described. Or, in a liquid electrical air freshener composition, it may be added at around 20% by weight based on the air freshener composition.

Accordingly, the present invention refers in a further aspect to a consumer product comprising an effective malodor-counteracting amount of a composition comprising bornyl or isobornyl acetate and at least one acid of Formula (I).

Another aspect of the invention are methods of removing malodor from the air or from surfaces, comprising contacting the source of said malodor with an effective amount of a composition comprising bornyl or isobornyl acetate and at least one acid of Formula (I) as hereinabove described. The methods can be, for example, spraying the ambient air surrounding the source of the malodors, or spraying an aerosol formulation directly onto the source of the malodor.

In a further aspect, the invention refers to a method of enhancing the malodor reduction properties of a consumer product, such as household products, and personal care products, comprising admixing to the product effective amounts of at least bornyl or isobornyl acetate and at least one acid of Formula (I) as hereinabove described.

Testing

A malodor evaluation panel of 14 persons was assembled and asked to evaluate the odor neutralizing effectiveness of bornyl acetate and of certain acids falling within the scope of Formula (I) in the molecular weight range of between 150 and 200, separately and in combination. The source of the malodor tested was cat urine.

Swatches of 100% untreated cotton fabric were cut into 15 cm (6-inch) squares and were placed on weighing boats. 0.5 grams of cat urine was pipetted onto each of the swatches. A period of three minutes was allowed for the urine to be absorbed by the fabric.

Onto each swatch, 3.0 grams of a composition was sprayed. As a control, 3.0 grams of water was sprayed on certain swatches.

Each swatch was placed in the middle of a two by two foot cubicle and all doors were closed. Actual testing was begun after thirty minutes.

Each member of the panel was asked to sniff the malodor control first and was notified that the control has a rating of 7—indicating very strong malodor. They were then asked to proceed to sniff the other samples and provide a rating for malodor remaining. Thus, the remaining malodor was evaluated on a sliding scale, with 1 being the absence of perceived malodor. The panelists were instructed to ignore any fragrance that they may detect and rate only for malodor.

For bornyl acetate alone and the acid of Formula (I) alone, the fabric sprays consisted of:
Test substance—1%
Neodol 91-8—1%
Fabric spray base—98%

For fabric sprays comprising both bornyl acetate and a subject acid, the formulation was:
Bornyl acetate—1%
Acid—1%
Neodol 91-8—2%
Fabric spray base—96.0%

Neodol 91-8 is a $C_9$-$C_{11}$ alcohol with an average of approximately 8 moles of ethylene oxide per mole of alcohol. The fabric spray base was an aqueous solution containing 10% ethanol, 1% of fragrance and 2% of non-ionic surfactant.

The results are shown in the following Table. Each panelist tested all of the acids, bornyl acetate and the combination. The scores reported are therefore the average of 14 replications.

TABLE

| Acid | Molecular Weight | Score Alone (at 1%) | Score in comb. with Bornyl Acetate (1% + 1%) | Bornyl Acetate (at 1%) | Score alone - score in comb. | Bornyl Acetate - score in comb. |
|---|---|---|---|---|---|---|
| Acetic Acid | 60.052 | 3.25 | 2.79 | 4.04 | 0.46 | 1.25 |
| Propionic Acid | 74.079 | 2.91 | 2.82 | 4.41 | 0.09 | 1.59 |
| Butyric Acid | 88.105 | 3.73 | 3.32 | 4.73 | 0.41 | 1.41 |
| Tiglic Acid | 100.116 | 4.18 | 3.29 | 3.82 | 0.89 | 0.54 |
| Hexenoic Acid | 114.142 | 3.33 | 2.75 | 4.25 | 0.58 | 1.50 |
| Caproic Acid | 116.158 | 2.88 | 2.71 | 3.75 | 0.17 | 1.04 |
| Cinnamic Acid | 148.159 | 3.63 | 3.29 | 4.46 | 0.33 | 1.17 |

The invention claimed is:

1. A malodor neutralizing composition, comprising:
   (1) bornyl acetate or isobornyl acetate, and
   (2) tiglic acid, hexenoic acid, or a monocarboxylic acid of the formula (I):

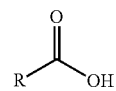

in which R is $C_1$-$C_3$ alkyl or $C_5$ alkyl,
   wherein the amount of ingredient (2) is 10-50% by weight of the total amount of ingredients (1) and (2), and the composition comprises from about 1% to about 20% by weight of a combination of ingredients (1) and (2).

2. A malodor neutralizing composition according to claim 1 in which ingredient (1) is bornyl acetate.

3. A malodor neutralizing composition according to claim 2 in which ingredient (2) is acetic acid, propionic acid, butyric acid, tiglic acid, hexenoic acid, or caproic acid.

4. A malodor neutralizing composition according to claim 3 in which ingredient (2) is butyric acid or hexenoic acid.

5. A perfumed product comprising a malodor neutralizing composition according to any of claim 1.

6. A perfumed product according to claim 5 in which ingredient (1) is bornyl acetate.

7. A perfumed product according to claim 6 in which ingredient (2) is acetic acid, propionic acid, butyric acid, tiglic acid, hexenoic acid, or caproic acid.

8. A perfumed product according to claim 7 in which ingredient (2) is butyric acid or hexenoic acid.

9. A household product comprising a malodor neutralizing composition according to claim 1.

10. A household product according to claim 9 in which ingredient (1) is bornyl acetate.

11. A household product according to claim 10 in which ingredient (2) is acetic acid, propionic acid, butyric acid, tiglic acid, hexenoic acid, or caproic acid.

12. A household product according, to claim 11 in which ingredient (2) is butyric acid or hexenoic acid.

13. A personal care product comprising a malodor neutralizing composition according to claim 1.

14. A personal care product according to claim 13 in which ingredient (1) is bornyl acetate.

15. A personal care product according to claim 14 in winch ingredient (2) is acetic acid, propionic acid, butyric acid, tiglic acid, hexenoic acid, or caproic acid.

16. A personal care product according to claim 15 in which ingredient (2) is butyric acid or hexenoic acid.

17. A method for reducing malodors which comprises contacting the source of said malodors with an effective amount of a malodor neutralizing composition comprising:

(1) bornyl acetate or isobornyl acetate, and
(2) tiglic acid, hexenoic acid, or a monocarboxylic acid of the formula (I):

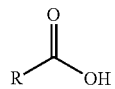

in which R is $C_1$-$C_3$ alkyl or $C_5$ alkyl,
wherein the amount of ingredient (2) is 10-50% by weight of the total amount of ingredients (1) and (2), and the composition comprises from about 1% to about 20% by weight of a combination of ingredients (1) and (2).

18. A method according to claim 17 in which ingredient (1) is bornyl acetate.

19. A method according to claim 18 in which ingredient (2) is acetic acid, propionic acid, butyric acid, tiglic acid, hexenoic acid, or caproic acid.

20. A method for reducing malodors emanating from household or personal care products which comprises admixing to said products a malodor neutralizing composition comprising (1) bornyl acetate or isobornyl acetate and (2) tiglic acid, hexenoic acid, or a monocarboxylic acid of the formula (I):

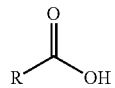

in which R is $C_1$-$C_3$ alkyl or $C_5$ alkyl,
wherein the amount of ingredient (2) is 10-50% by weight of the total amount of ingredients (1) and (2), and the composition comprises from about 1% to about 20% by weight of a combination of ingredients (1) and (2).

21. A method according to claim 20 in which ingredient (1) is bornyl acetate.

22. A method according to claim 21 in which ingredient (2) is acetic acid, propionic acid, butyric acid, tiglic acid, hexenoic acid, or caproic acid.

* * * * *